(12) United States Patent
Pagán

(10) Patent No.: US 9,526,659 B2
(45) Date of Patent: Dec. 27, 2016

(54) H2O CILIA HEAD SWAB

(71) Applicant: Beniamino Pagán, Guayanilla, PR (US)

(72) Inventor: Beniamino Pagán, Guayanilla, PR (US)

( * ) Notice: Subject to any disclaimer, the term of this patent is extended or adjusted under 35 U.S.C. 154(b) by 0 days.

(21) Appl. No.: 14/215,309

(22) Filed: Mar. 17, 2014

(65) Prior Publication Data

US 2015/0257933 A1    Sep. 17, 2015

(51) Int. Cl.
| | | |
|---|---|---|
| *A61F 13/15* | (2006.01) | |
| *A61F 13/20* | (2006.01) | |
| *A61F 11/00* | (2006.01) | |
| *A61F 13/38* | (2006.01) | |

(52) U.S. Cl.
CPC ............ *A61F 11/006* (2013.01); *A61F 13/38* (2013.01)

(58) Field of Classification Search
CPC .................................................. A61F 11/006
USPC ........................................................ 606/162
See application file for complete search history.

(56) References Cited

U.S. PATENT DOCUMENTS

| | | | |
|---|---|---|---|
| 1,980,826 A * | 11/1934 | Reiss ............................ 606/161 |
| 3,923,061 A * | 12/1975 | Rossignol ................ A47K 7/00 600/572 |
| 4,073,937 A * | 2/1978 | Van Cleave ........... A61K 31/74 424/616 |
| 4,940,454 A | 7/1990 | Siragusa | |
| 5,147,288 A | 9/1992 | Schiavo | |
| 5,300,018 A | 4/1994 | Walsh | |
| D358,646 S * | 5/1995 | Weber .......................... D24/149 |
| 5,548,862 A | 8/1996 | Curtis | |
| 5,715,850 A * | 2/1998 | Markgraaf ............ A61F 11/006 132/333 |
| 5,954,682 A | 9/1999 | Petrus | |
| 6,413,087 B1 | 7/2002 | Broyles et al. | |
| D489,131 S * | 4/2004 | Gojcaj ........................ D24/147 |
| 6,725,568 B2 | 4/2004 | Gronka | |
| 6,939,360 B2 * | 9/2005 | Crespo .................. A61F 11/006 606/162 |
| 7,008,392 B2 * | 3/2006 | Beaudry ........................... 604/1 |
| 7,097,629 B2 | 8/2006 | Blair | |
| 7,481,006 B2 | 1/2009 | Donovan | |
| 7,789,845 B1 | 9/2010 | Meliti | |
| 8,241,236 B2 | 8/2012 | Yardley | |
| 8,551,031 B2 | 10/2013 | Aubin-Edme et al. | |
| 8,777,972 B2 * | 7/2014 | Burres .................. A61F 11/006 606/162 |
| 8,784,352 B2 | 7/2014 | Huttner | |
| 9,233,027 B1 * | 1/2016 | Jackson ................ A61F 11/006 |
| 2005/0154342 A1 | 7/2005 | Cyn | |

(Continued)

FOREIGN PATENT DOCUMENTS

EP    1504722    *  2/2005   ............. A61B 10/00

OTHER PUBLICATIONS

Puritan Medical Products Co. LLC, Puritan Diagnostic Swabs, Jul. 2013.*

(Continued)

*Primary Examiner* — Michele M Kidwell
(74) *Attorney, Agent, or Firm* — Eugenio J. Torres-Oyola; Jose A. Medina-Cruz; Ferraiuoli LLC

(57) ABSTRACT

A hydrophilic swab comprised of microcilios to transport water out of the ear canal in an "osmotic" fashion. The invention includes an enabling gyratory mechanism that impulses the cilia into the ear, and it also displays a water absorption-level indicator.

3 Claims, 2 Drawing Sheets

(56) References Cited

U.S. PATENT DOCUMENTS

| | | | |
|---|---|---|---|
| 2007/0183986 A1* | 8/2007 | Allred | A61K 8/21 |
| | | | 424/52 |
| 2007/0255175 A1* | 11/2007 | Sangha | 600/572 |
| 2007/0299457 A1* | 12/2007 | Morales | A61F 11/006 |
| | | | 606/162 |
| 2008/0142385 A1* | 6/2008 | Stein et al. | 206/362 |
| 2008/0208100 A1 | 8/2008 | Wolff | |
| 2009/0112241 A1* | 4/2009 | Bar et al. | 606/162 |
| 2010/0305540 A1 | 12/2010 | Huttner | |
| 2011/0066172 A1* | 3/2011 | Silverstein | 606/162 |
| 2011/0270290 A1 | 11/2011 | Friedman et al. | |

OTHER PUBLICATIONS

Puritan Meidcal, Product Brochures, http://www.puritanmedproducts.com/resources/product-brochures (accessed Mar. 17, 2016).*

* cited by examiner

H2O CILIA HEAD SWAB

RELATED APPLICATIONS

This application claims the benefit of U.S. Provisional Application No. 61/800,086 filed Mar. 15, 2013, which is hereby incorporated by reference in its entirety.

STATEMENT REGARDING FEDERALLY SPONSORED RESEARCH AND DEVELOPMENT

N/A

REFERENCE TO SEQUENCE LISTING, A TABLE, OR A COMPUTER PROGRAM LISTING COMPACT DISK APPENDIX

N/A

TECHNICAL FIELD

The present invention is in the technical field of means for cleaning eye, ear or nose. More particularly, the present invention is in the technical field of swabs including handle (e.g., stick, etc.) with absorbent material at end thereof.

BACKGROUND OF THE INVENTION

Affecting the outer ear, swimmer's ear is a painful condition resulting from inflammation, irritation, or infection. These symptoms often occur after water gets trapped in the ear, with subsequent spread of bacteria or fungal organisms. Because this condition commonly affects swimmers, it is known as swimmer's ear. Swimmer's ear (also called acute otitis externa) often affects children and teenagers, but can also affect those with eczema (a condition that causes the skin to itch), or excess earwax.

A common source of the infection is increased moisture trapped in the ear canal, from baths, showers, swimming, or moist environments. When water is trapped in the ear canal, bacteria that normally inhabit the skin and ear canal multiply, causing infection of the ear canal. Swimmer's ear needs to be treated to reduce pain and eliminate any effect it may have on your hearing, as well as to prevent the spread of infection.

Other factors that may contribute to swimmer's ear include:
  Contact with excessive bacteria that may be present in hot tubs or polluted water
  Excessive cleaning of the ear canal with cotton swabs or anything else
  Contact with certain chemicals such as hair spray or hair dye (Avoid this by placing cotton balls in your ears when using these products.)
  Damage to the skin of the ear canal following water irrigation to remove wax
  A cut in the skin of the ear canal
  Other skin conditions affecting the ear canal, such as eczema or seborrhea The most common symptoms of swimmer's ear are itching inside the ear and pain that gets worse when you tug on the auricle (outer ear). Other signs and symptoms may include any of the following:
  Sensation that the ear is blocked or full
  Drainage
  Fever
  Decreased hearing
  Intense pain that may spread to the neck, face, or side of the head
  Swollen lymph nodes around the ear or in the upper neck.
  Redness and swelling of the skin around the ear If left untreated, complications resulting from swimmer's ear may include:
  Hearing loss. When the infection clears up, hearing usually returns to normal.
  Recurring ear infections (chronic otitis externa). Without treatment, infection can continue.
  Bone and cartilage damage (malignant otitis externa). Ear infections when not treated can spread to the base of your skull, brain, or cranial nerves. Diabetics and older adults are at higher risk for such dangerous complications.

Although external otitis can be treated by applying antibiotic drops, it is preferable to prevent it from occurring in the first place. Removing water as soon as possible can prevent the series of conditions that lead to swimmer's ear.

There are several methods for achieving this result. Generally, people tend to use common cotton swabs to remove the water inside the ears. However, common swabs cannot be inserted inside the ears deeply enough to remove the water effectively. And when they are forced inside the ear, the cause pain and tend to leave cotton residue inside the ear, worsening the condition.

All in all, current options available in the market for tackling this issue are either ineffective or prone to lacerate and/or damage the ear canal.

U.S. patent application No. US 20050154342 A1 discloses a conical swab for removal of water inside the ears, This invention doesn't have a water absorption indicator like the present one, so it is not difficult to know when the water has been absorbed. This swab also has a thin pointed end that could be harmful to the ear canal if forced inside.

U.S. Pat. No. 6,725,568 discloses an ear canal dryer. This invention only removes liquid from the outer ear canal and cannot be inserted deeply into the ear. Its shape does not let it go deeper inside the ear canal, preventing it from removing water from the inner part of the canal.

U.S. patent application No. US 20100305540 discloses a device and a method to prevent swimmer's ear. This invention cannot be inserted so deep in the ear canal and only extracts liquid from the external part of the ear. Its shape does not let it go deeper inside the ear canal, preventing it from removing water from the inner part of the canal.

All in all, current options available in the market for tackling this issue are either ineffective or prone to lacerate and/or damage the ear canal.

Accordingly, there remains a need for an improved head swab that is effective, that can be inserted deep into the ear canal without causing pain or damage, and that indicate when the water has been absorbed effectively to overcome the disadvantages and shortcomings of the prior art.

SUMMARY OF THE INVENTION

The invention disclosed herein is directed to a hydrophilic swab stick device comprising an extension element rod comprising an elongated body having a proximal end and a distal end. The proximal end comprises an oval capsule divided into two sections referred to herein as a cilia capsule and a pivot capsule. The cilia capsule is located towards the proximal end of the elongated body and comprises absorbent filaments. The absorbent filaments protrude and retract from the cilia capsule when engaged by a gyratory mechanism contained in the extension element rod.

The pivot capsule encapsulates a spongy body having an absorbent head and an absorbent body. The absorbent body fills the interior of the extension element rod. The absorbent filaments are connected to the spongy body. The distal end comprises a sealed end.

The invention disclosed herein can be largely described as a device intended to remove water accumulated inside the ear canal. The system includes a small head comprised of a series of ultra-soft and absorbent microcilios (or the "cilia") that, when rotated by 360 degrees, open up into the auditory conduit. The cilia are connected to a spongy head and reach the ear canal through a cavity. They are covered by a capsule (cilia capsule), partly plastic and partly rubbery. This capsule is divided into two segments by a rotary channel, which allows for both rotational and pivotal functions. The capsule displays a smooth and hollow plastic extension with a sealed end in the side that opposes/faces the cilia head. This extension is filled with a spongy and absorbent or cavernous body for the storage and retention of water or liquid excess, which also works as a holder to enable the rotation of the device by a simple act of manipulation. This frame also features a tiny window or indicator located nearby the cilia capsule (inside the gyratory mechanism) which is intended to indicate when the liquid has been absorbed.

In essence, the present invention relates to a hydrophilic swab comprised of microcilios to transport water out of the ear canal in an "osmotic" fashion. The hydrophilic material constituting the cilia are intended to act as "micro water suction fingers". The cilia in this swab are "hairlike" structures that avoid the laceration or damaging of the ear drum. This product also features a gyratory mechanism for enabling the insertion of the cilia into the ear canal and a tiny window or indicator located nearby the cilia capsule (in the manipulation extension) intended to indicate when the liquid has been absorbed.

The H2O Cilia Swabs prevent ear infections and other complications by removing water accumulated in the ear canal, and maintaining the passage cleaner and free from excessive moisture. This invention is intended to promptly and safely solve the problem of the discomfort associated to standing water in the ear canal that could cause imbalance. By using "hairlike" microcilios as the hydrophilic material, laceration and/or damaging of the ear canal can be prevented.

DETAILED DESCRIPTION OF THE INVENTION

Figure 1:
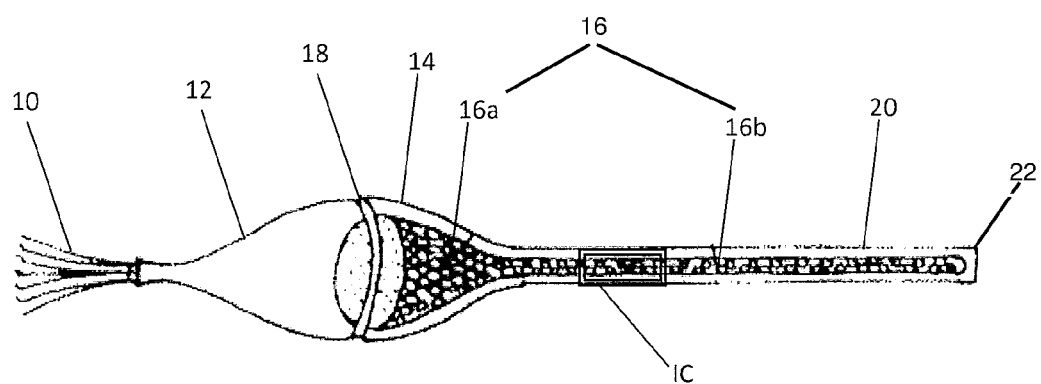
FIG. 1 is a perspective view, showing the present invention.

FIG. 1 shows a perspective view of the present invention. The microcilios 10 are "hairlike" micro suction fingers or filaments made from soft ultra absorbent-material. Their primary function is to absorb liquid accumulation in the auditory canal, to alleviate discomfort and infection potential. The microcilios 10 (also referred to herein as absorbent filaments) protrude from an opening in an oval capsule composed of a pivot capsule 12 and a cilia capsule 14. Specifically, the microcilios 10 protrude from a small opening 24 located at the extreme end of the pivot capsule 12. The pivot capsule 12 and cilia capsule 14 are held together by a rotary channel 18 that allows for both rotational and pivotal functions. The cilia capsule 14 connects at its lower end with the extension element rod 20 of the present invention that serves as a handle that enables projection of the microcilios 10 by rotational manipulation. Inside the cilia capsule 14 and the extension element rod 20 the device is filled with a reservoir sponge 16 whose main function is to provide liquid retention capacity and storage for the liquid captured by the microcilios 10. At the opposite end of the cilia capsule 14, the exement rod 20 comprises a sealed end 22. The reservoir sponge or spongy body, comprised of an absorbent head 16a and an absorbent body 16b, serves as a storage medium for the liquid until it is disposed of A tiny window or liquid indicator IC, is located nearby the cilia capsule (inside the gyratory mechanism) and it is intended to indicate when the liquid has been absorbed.

Figure 2:
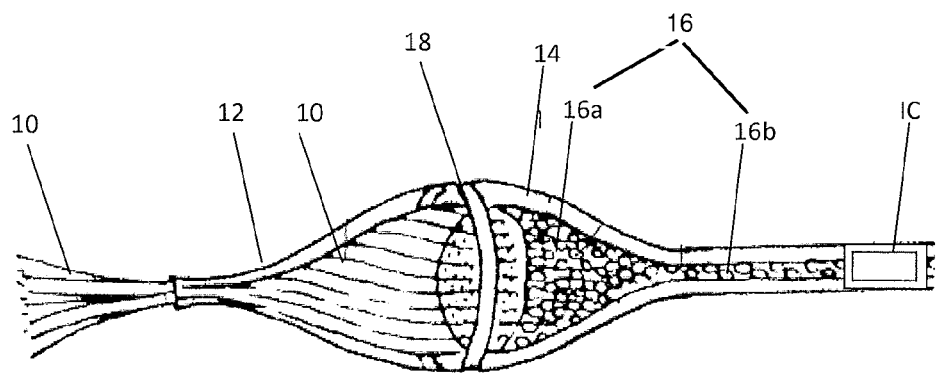
FIG. 2 is a closer perspective view, showing in detail the cilia capsule embodiment of the invention.

FIG. 2 depicts a closer perspective view that shows in detail the cilia capsule embodiment of the invention. In this illustration it can be better observed the relationship and connectivity between the microcilios 10 and the reservoir sponge absorbent head 16a. These two elements, microcilios 10 and reservoir sponge absorbent head 16a, interconnect at a point just below the rotary channel 18. The location of the reservoir sponge absorbent head 16a and the rotary channel 18 allows for easy manipulation of the projection of the microcilios by twisting and maneuvering the extension 20. The delicate complexion of the microcilios 10 allows for liquid or water absorption deep into the auditory canal without risk of perforation or laceration to the eardrum. The design of the upper extreme of the pivot capsule 12, from where the microcilios 10 protrude, keeps the solid elements of the present invention from entering the auditory canal.

Figure 3:
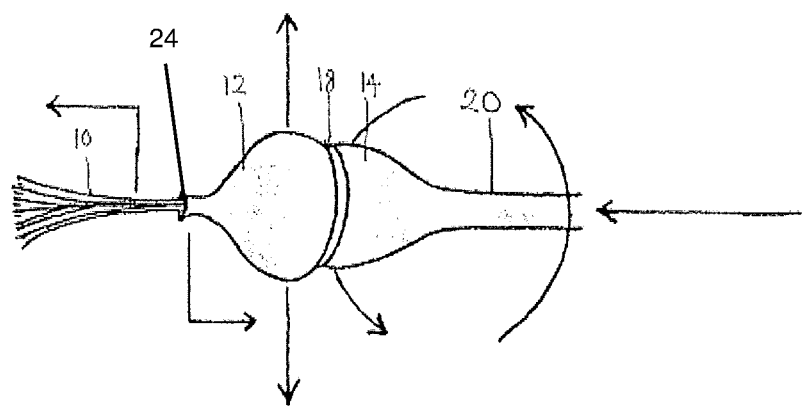
FIG. 3 is a perspective view, illustrating the movement and functionality of some embodiments in the present invention.

FIG. 3 is a perspective view, which illustrates the movement and functionality of some of the embodiments of the present invention. This figure shows that through the twisting and manipulation of the extension 20 the rotary channel 18 contained in the capsule enables control of the projection of the microcilios 10. The upward or downward movement of the extension 20 allows pivotal control of the microcilios 10 for better and more complete access to accumulated liquid in the auditory canal. The manner in which the microcilios 10 open in a "fanlike" fashion enables the present invention to maximize the performance of the liquid or water absorption.

Having described my invention in detail, what I claim is:
1. A hydrophilic swab stick device comprising:
   an extension element rod comprising an elongated body having a proximal end and a distal end;
   said proximal end comprising a cilia capsule, said cilia capsule being held together to a pivot capsule by a rotary channel, said pivot capsule comprising a small opening and a plurality of microcilios protruding from said small opening;
   said distal end comprising a sealed end;
   a liquid indicator; and
   a reservoir sponge, wherein said reservoir sponge comprises an absorbent head and absorbent body;
   wherein said extension element rod is filled with said absorbent body;
   wherein said cilia capsule encapsulates said absorbent head;
   wherein said plurality of microcilios are connected to the reservoir sponge;

wherein the rotary channel enables control of the projection of the plurality of microcilios through manipulation of the extension element rod; and wherein the upward or downward movement of the extension element rod allows pivotal control of the plurality of microcilios.

2. The hydrophilic swab stick device according to claim 1, wherein the cilia capsule is made partly of plastic and partly of rubber.

3. The hydrophilic swab stick device according to claim 1, wherein the plurality of microcilios are configured to open up inside an auditory conduit in a circular configuration.

* * * * *